United States Patent
Keller et al.

(10) Patent No.: US 7,144,846 B2
(45) Date of Patent: Dec. 5, 2006

(54) ACIDIC PHENOLIC DISINFECTANT COMPOSITIONS

(75) Inventors: Shahin Keller, St. Louis, MO (US); Herbert J. Kaiser, Pontoon Beach, IL (US); Jason F. Tirey, Chesterfield, MO (US); Daniel A. Klein, Shiloh, IL (US); Nancy E. Kaiser, Pontoon Beach, IL (US)

(73) Assignee: Steris, Inc., Temecula, CA (US)

( * ) Notice: Subject to any disclaimer, the term of this patent is extended or adjusted under 35 U.S.C. 154(b) by 0 days.

(21) Appl. No.: 10/843,600

(22) Filed: May 11, 2004

(65) Prior Publication Data

US 2005/0256018 A1    Nov. 17, 2005

(51) Int. Cl.
*C11D 3/48* (2006.01)
*C11D 7/26* (2006.01)
*C11D 3/44* (2006.01)

(52) U.S. Cl. ............. 510/161; 510/130; 510/131; 510/132; 510/138; 510/191; 510/238; 510/253; 510/386; 510/387; 510/388; 510/477; 510/432

(58) Field of Classification Search ........ 510/130, 510/131, 132, 138, 161, 191, 238, 253, 386, 510/387, 388, 477, 432
See application file for complete search history.

(56) References Cited

U.S. PATENT DOCUMENTS

| | | | | |
|---|---|---|---|---|
| 4,157,977 A | * | 6/1979 | Dewar et al. | 510/386 |
| 4,654,374 A | * | 3/1987 | Martin | 514/698 |
| 4,808,410 A | * | 2/1989 | Sorrentino et al. | 424/435 |
| 5,620,655 A | * | 4/1997 | Nevermann | 422/28 |
| 5,635,462 A | * | 6/1997 | Fendler et al. | 510/131 |
| 5,696,170 A | * | 12/1997 | Exner et al. | 514/693 |
| 5,816,446 A | * | 10/1998 | Steindorf et al. | 222/1 |
| 5,955,408 A | * | 9/1999 | Kaiser et al. | 510/131 |
| 5,962,001 A | * | 10/1999 | Rose et al. | 424/404 |
| 6,106,851 A | * | 8/2000 | Beerse et al. | 424/401 |
| 6,183,757 B1 | * | 2/2001 | Beerse et al. | 424/401 |
| 6,183,763 B1 | * | 2/2001 | Beerse et al. | 424/404 |
| 6,333,006 B1 | * | 12/2001 | Vellutato | 422/22 |
| 6,358,906 B1 | * | 3/2002 | Ochs et al. | 510/382 |
| 6,413,921 B1 | * | 7/2002 | Childers et al. | 510/131 |
| 6,616,922 B1 | * | 9/2003 | Taylor et al. | 424/70.28 |

\* cited by examiner

*Primary Examiner*—Charles Boyer
(74) *Attorney, Agent, or Firm*—Hudak, Shunk & Farine, Co. LPA

(57) ABSTRACT

A low pH disinfectant composition comprises an aqueous composition of a phenolic compound, an organic acid, and/or a dispersing surfactant and/or solvent. The disinfectant solution can be concentrated, or more preferably diluted ready to use, and is very effective in eradicating fungi including *Aspergillus niger*.

41 Claims, No Drawings

ACIDIC PHENOLIC DISINFECTANT COMPOSITIONS

FIELD OF THE INVENTION

A ready-to-use aqueous phenolic disinfectant comprises a phenolic compound, an organic acid, and a dispersing agent to provide very effective activity against viruses, bacteria, and fungi including *Aspergillus niger*.

BACKGROUND OF THE INVENTION

Heretofore, various disinfectants including phenolic disinfectants have been utilized to disinfect various items and objects. However, no known acidic phenolic disinfectant exists which shows complete activity against *Aspergillus niger*. Moreover, ready-to-use (RTU), sterile phenolic disinfectants are currently not available and must be made from a concentrated sterile solution diluted with water. To produce a sterile product for an end use, the customer must dilute a concentrated solution in a clean room. The customer needs to validate the dilution along with aseptic assembly and blending. For non-sterile products, the customer must sterile filter the disinfectant solution into the clean room, but this does not meet the industry standard of sterility. The customer must also validate the procedure. This requires a high level of documentation and is a very time consuming and labor intensive activity.

Disinfectants are applied to inanimate objects and surfaces to kill or irreversibly inactivate bacteria, pathogenic fungi, viruses and other undesirable infectious microorganisms. Disinfectants are commonly used in hospital and medical related areas generally including clinics, medical centers, pharmaceutical facilities, and clean rooms. Disinfectants can also be used in homes as in bathrooms, showers, and other non-food areas. Phenol and phenol derivatives have been used as disinfectants.

SUMMARY OF THE INVENTION

It now has been found that a RTU sterile disinfecting composition based on an aqueous dispersed phenolic compound can be produced for direct use without necessitating the end user to first dilute and/or sterilize the phenolic disinfecting composition. Aqueous phenolic compound compositions containing an effective amount of organic acid provides considerably improved disinfecting activity and also aids in stabilizing the phenolic composition. RTU dilute aqueous disinfectants can be used directly by the end user to kill various forms of viruses, bacteria, and pathogenic fungi. The disinfectant compositions of the present invention are also readily effective in killing the most resistant fungi organism known, *Aspergillus niger*.

The aqueous disinfectant of this invention comprises the combination of a phenolic compound and one or more organic acids generally having a $pK_a$ of at least 1.0 in a sufficient amount to produce an acidic composition. Dispersing agents such as surfactants and/or alcohols, and/or simple glycols are utilized to solubilize the phenolic compound in water. The aqueous disinfectant can be formulated such that it is a RTU phenolic disinfectant.

DETAILED DESCRIPTION OF THE INVENTION

The disinfecting composition of this invention is based on a phenolic compound disposed in water along with additive amounts of organic acid and solubilizing agent. For purposes of this invention, a phenolic compound comprises phenol, that is a hydroxyl group attached directly to a benzene ring carbon, and derivatives of phenol. Phenol derivatives include substituted phenols having at least one substitute group(s) attached to at least another ring carbon atom of the phenol. The substituted group frequently increases activity of the phenol. Substituted groups include at least one hydrocarbon group such as an aliphatic (e.g. alkyl), an aromatic or combinations thereof having from 1 or 6 to about 20 and desirably from 2 or 6 to about 10 carbon atoms, halogen, a nitrogen containing group such as an amine or a nitro, hydroxyl, similar substituted groups, and combinations thereof.

Useful phenolic compounds include phenol; cresols; alkyl and dialkyl phenols; dihydric phenols such as catechol, resorcinol, and hydroquinone; alkyl dihydroxybenzenes; halogen substituted phenols, such as chlorophenols, alkyl and/or aromatic substituted chlorophenols; nitrophenols, dinitrophenols, trinitrophenols, and alkyl or aromatic substituted nitrophenols; aminophenols; aromatic, alkyl aromatic, and aromatic alkyl substituted phenols; hydroxybenzoic acids; bisphenols, bis(hydroxyphenyl) alkanes, and hydroxyquinolines such as 8-hydroxyquinoline. Phenolic compounds preferred as disinfectants include o-phenylphenol (OPP), p-t-amylphenol (PTAP), o-benzyl-p-chlorophenol (OBPCP), p-chloro-m-xylenol (PCMX), 5-chloro-2-(2,4-dichlorophenoxy)phenol (Triclosan) and the like.

The amount of phenolic compound, as well as the various other components of the RTU disinfectant composition of the present invention will be based upon 100 parts by weight of water for ease of describing the invention. For a RTU composition, the total amount of one or more phenolic compounds is from about 0.005 to about 16, desirably from about 0.007 to about 5.0, and preferably from about 0.01 to about 0.2 or about 0.3 parts by weight for every 100 parts by weight of water of a RTU composition.

To achieve very effective aqueous phenolic disinfectant compositions, an important aspect of the present invention is to utilize acidic solutions containing one or more weak organic acids. The pH of the aqueous disinfectant compositions of the present invention is less than 7.0, desirably from about 1 to about 6, and preferably from about 2 or about 3 to about 5. Weak organic acids are desired such as those that have a $pK_a$ of from about 1 to about 6.5, and preferably from about 3.0 to about 5.0. Although only one weak organic acid can be utilized, desirably two or more such acids are used in combination. Examples of weak organic acids generally include simple monocarboxylic acids and dicarboxylic acids having generally from 1 to about 10 carbon atoms and preferably from 1 to about 6 carbon atoms. Specific examples include formic acid, acetic acid, propionic acid, acrylic acid, butyric acid, isobutyric acid, crotonic acid, valeric acid, isovaleric acid and citric acid. Other simple carboxylic acids include hydroxyl containing carboxylic acids such as lactic acid, and glycolic acid. Simple carboxylic acids containing five carbon atoms or less are preferred because of their good solubility in water.

Dicarboxylic acids can be utilized containing from 2 to about 7 carbon atoms and desirably from 2 to about 5 carbon atoms since they have good solubility in water. Examples of dicarboxylic acids include oxalic acid, malonic acid, succinic acid, glutaric acid, adipic acid, pimelic acid, maleic acid, fumaric acid and citric acid.

Preferred weak organic acids include formic acid, acetic acid, lactic acid, glycolic acid, citric acid, and the like.

The amount of weak organic acids is generally an amount which renders the aqueous disinfectant composition acidic and thus within the above-noted pH ranges desirably of about 1 to about 6 and preferably from about 2 to about 5. Effective total amounts of the one or more weak organic acids are generally from about 0.5 or about 2 or about 3 to about 30 parts by weight and desirably from about 5 to about 17 or about 20 parts by weight for every 100 parts by weight of water.

Non-organic acids are generally avoided inasmuch as they do not yield good activity with regard to microorganisms. Accordingly, the disinfectant compositions of the present invention are preferably free of inorganic acids such as phosphoric acid, nitric acid, hydrochloric acid, and sulfuric acid. If utilized, the amount of such acids is very low such as less than about 1 part by weight, and desirably less than about 0.5 parts by weight for every 100 parts of water in the disinfectant composition of the present invention.

Phenolic compounds generally have poor water solubility under the required acidic conditions of the present invention. To provide a stable aqueous disinfectant, a dispersing agent such as a surfactant and/or a solvent is utilized to solubilize the phenolic compound and to provide adequate wetting properties.

Considering the surfactants, generally any surfactant can be utilized which solubilizes a necessary amount of the phenolic compound to obtain a desired activity against a virus, a bacteria, or a fungi. A great number of classes and specific surfactants can be utilized including various anionic surfactants, various cationic surfactants, various amphoteric surfactants, as well as various nonionic surfactants. Examples of such surfactants are set forth in 2003 McCutheon's Volume 1: Emulsifiers & Detergents (The Manufacturing Confectioner Publishing Company; Glen Rock, N.J.). Whether a surfactant is suitable or not can be readily determined by adding various amounts to the above blend of water, phenolic compound, and organic acid. While nonionic surfactants are desired, anionic surfactants are generally more desired and ordinarily comprise alkyl hydrophobic hydrocarbon chains having terminal anionic hydrophilic polar groups such as carboxylate, sulfonate, sulfate, phosphonate and phosphate polar groups. The alkyl can contain from about 2 to about 24 carbon atoms and desirably from about 8 to about 20 carbon atoms. Preferred surfactants comprise fatty acid chains containing about 10 to about 20 carbon atoms and may contain one or more double bonds, if desired, as in naturally occurring fatty acid vegetable oils. Carboxylate surfactants ordinarily comprise alkyl hydrocarbon hydrophobic chains whereas sulfonate surfactants comprise alkyl, aryl, or alkyl-aryl hydrophobic chains which may contain double bonds, ester or amide groups.

Desired surfactants include the following: Sodium Caprylamphopropionate (Miranol JEM), Sodium 2-ethylhexyl sulfate (Rhodapon BOS, Sulfotex OA), sodium octyl sulfate (Standapol LF), Sultech 2113, Disodium Cocoamphodiacetate (Mackam 75/2C), Disodium Capryloamphodipropionate (Mackam 2CYSF), Cocamidopropyl Hydroxysultaine (Mackam CBS 50), Sodium Capryloamphohydroxypropylsufonate (Mackam JS), Caprylamidopropyl Betaine (Mackam OAB, DV 6836), methyl ester soybean oil (Septosol SB-D), Diphenylene Oxide Disulfonate (Rhodacal DSB), Lauraminopropionic Acid (Deriphat 151C), alkylpolyglucosides (Glucopon 425), Sodium laurylether sulfate (SLES), Octylamine Oxide (Mackamine C-8), octyl betaine (Mackam BW 139), Sodium Alkyl Naphthalene Sulfonate (Petro ULF), linear alkylbenzene sulfonates (Biosoft S-101), Lauramine Oxide, alkylamine oxides (AO 728), alkylether sulfonates (Avanel S-74), anionic and nonionic fluorosurfactants (Zonyl FS-62, Zonyl FSH, Zonyl FSP, Zonyl 9361), cationic/nonionic surfactant blends (Burcoterge CSB), alkylpolyglucosides (AG 6202), tall oil based amides (Burcoimidozoline), propoxylated and ethoxylated fatty acids (Burcoterge LFE 1000), modified ethoxylated carboxylates (Deterge LF 7315), phosphated amphoterics (Deteric CSP), ethoxylated complex amines (Deterge AT 100), diphenyl sulfonate derivatives (Dowfax 8390), phosphate esters (Colatrope 555, Colafax 3373 PE, Colafax 3371 PE), alkylether hydroxysultaines (Mirataine ASC), anionic proprietary blends (Colonial ZF 20), diphenyl sulfonate derivatives (Surfedon LP 300), organic phosphated amphoteric (Deteric CSP), salts of N-lauryl beta iminodiproprianate (Deriphat 160C), iminodipropionate amphoteric (Amphoteric 400), proprietary hydrotropes (Monatrope 1250), Cocamide DEA (Ninol 40-CO) and dodecylbenzene sulfonic acid (Biosoft S 101), wherein the number of carbon atoms in the alkyl group is as noted above.

Preferred surfactants include the various fluorosurfactants such as the above noted Zonyl® compounds made by Dupont which generally contain an anionic group, a substantially hydrocarbon portion such as a polyether having from 1 to 3 or 4 carbon atoms as well as a fluorinated alkyl group including perfluorinated alkyl groups where R is generally from about 5 to about 15 carbon atoms. More specifically, the following Zonyl® fluorosurfactants can be utilized.

| Zonyl® | Chemical Structure | | Ionic Type |
|---|---|---|---|
| Anionic Fluorinated Surfactants | | | |
| FSP | $(R_fCH_2CH_2O)_xPO(O^-NH_4^+)_y$ | $x + y = 3$ | Anionic |
| 9361 | $(R_fCH_2CH_2O)_xPO(O^-NH_2^+[CH_2CH_2OH]_2)_y$ | $x + y = 3$ | Anionic |
| FSE | $(R_fCH_2CH_2O)_xPO(O^-NH_4^+)_y(OCH_2CH_2OH)_z$ | $x + y + z = 3$ | Anionic |
| FS-62 | $C_6F_{13}CH_2CH_2SO_3H$, $C_6F_{13}CH_2CH_2SO_3^-NH_4^+$ | | Anionic |
| FSA | $R_fCH_2CH_2S\ CH_2CH_2COO^-Li^+$ | | Anionic |
| Nonionic Fluorinated Surfactants | | | |
| FSH | $R_fCH_2CH_2O(CH_2CH_2O)_wH$ | | Nonionic |
| FSO | $R_fCH_2CH_2O(CH_2CH_2O)_xH$ | | Nonionic |
| FSN | $R_fCH_2CH_2O(CH_2CH_2O)_yH$ | | Nonionic |
| FS-300 | $R_fCH_2CH_2O(CH_2CH_2O)_zH$ | $w < x < y < z$ | Nonionic |

-continued

| Zonyl ® | Chemical Structure | Ionic Type |
|---|---|---|
| Fluorosurfactants | | |
| FSN-100 | $R_fCH_2CH_2O(CH_2CH_2O)_yH$ | Nonionic |
| FSO-100 | $R_fCH_2CH_2O(CH_2CH_2O)_xH$ | Nonionic |
| FSG | Polymeric fluorochemical | Nonionic |
| FTS | $R_fCH_2CH_2OOCC_{17}H_{35}$ (Stearate) | Nonionic |
| FBC | $R_fCH_2CH_2OOC)_3C_3H_5O$ (Citrate) | Nonionic |

$R_f = CF_3CF_2(CF_2CF_2)_n$, where n = 2–4

Effective total amounts of one or more surfactants generally range from about 0.01 or about 0.02 to about 10 or about 15, and desirably from about 0.05 to about 1 or about 3 parts by weight per 100 total parts by weight of water.

In lieu of or in combination with a surfactant, a solubilizing solvent such as a glycol or an alcohol can be utilized. Useful glycols are low molecular weight alkyl glycols generally having from 2 to about 10 or about 12 carbon atoms and include alkylene and diether glycols. Examples of suitable glycols include ethylene glycol, propylene glycol, hexylene glycol, 1-butoxyethanol, ethylene glycol n-butyl ether, diethylene glycol monoethyl ether, diethylene glycol monobutyl ether, dipropylene glycol monomethyl ether, N-methyl-2-pyrolidone.

Useful alcohols can be saturated lower alkyl alcohols containing from 1 to about 10 carbon atoms with from about 2 to about 4 carbon atoms being preferred. Specific examples of useful alcohols include methanol, ethanol, n-propyl, isopropyl (highly preferred), n-butyl, sec-butyl, t-butyl alcohols as well as N-methyl-2-pyrolidone and phenoxyethanol.

The total amount of the one or more solvents such as an alcohol and/or a glycol is from about 0.5 or about 1.0 to about 20 or about 30, and desirably from about 1.5 to about 8 or about 15 parts by weight per 100 total parts by weight of water.

The total amount of the one or more dispersing agents be it a surfactant, or an alcohol, or both, is generally from about 0.01 to about 45 parts by weight, and desirably from about 1.5 or about 2.0 to about 10 or about 20 parts by weight for 100 parts by weight of water.

Various conventional additives can be utilized in conventional amounts such as colorants or dyes, deodorizers, odor masking agents, perfumes, thickening agents, corrosion inhibitors, and the like.

The aqueous disinfectant compositions of the present invention can be readily prepared depending on whether the phenolic compound is a solid or liquid. If solid phenols are used, the solid phenolic can be first dissolved in the solvent or solvents to form a phenolic compound premix. The appropriate amount of water can be weighed in a separate vessel. The surfactants then can be added to the water with agitation. The phenolic premix then can be added to the water and surfactant mixture and mixed until uniform. The organic acid or acids then can be added to the mixture and mixed thoroughly.

In an alternative preparation, the appropriate amount of water and surfactant can be mixed in a vessel. A commercially available liquid phenolic, such as a (75% phenolic, 25% isopropyl alcohol mixture), is then added with mixing. The organic acid or acids then can be added and mixed until uniform.

The various additives can then be added. The aqueous disinfectant composition is ready to use as is. No further treatment or dilution is necessary, except for sterilization if desired.

A concentrated form of the aqueous disinfectant, as opposed to an RTU form, can be prepared by first dissolving the phenolic in a solvent or solvents and mixing with from about 2% or about 3% to about 40% or about 50%, or about 75%, or about 90%, or about 99% by weight of the appropriate water weight, optionally containing a surfactant. The acid can be added last. This concentrate can then be subsequently used for in-line preparation of the product by adding the appropriate remaining amount of water. Stated differently, in the above description the amount of water utilized in the concentrate can be reduced from 100 parts by weight to about 2 to or about 3 to about 40 or about 50, or about 75, or about 90, or about 99 total parts by weight and desirably from about 30 to about 40 total parts by weight of water. Accordingly the amount of the various components such as the phenol compound, the organic acid, and dispersing agent will be proportionally increased.

The aqueous disinfectant compositions of the present invention, while being an extremely effective RTU, optionally but not desirably, can be irradiated such as through the use of gamma radiation, because of various industry standards concerning sterile disinfectants. Gamma radiation of the ready-to-use disinfectant compositions can be carried out at various dosage ranges expressed in Kilogray (KGy). The doses can be controlled by adjusting exposure times. Suitable KGy can be from about 10 to about 50 KGy and any ranges therebetween such as from about 15 to about 20 and/or about 30 to about 40 KGy. Such radiation procedures are known to the literature and to the art. Ionizing x-ray radiation can be used if desired.

The ready-to-use aqueous disinfectant compositions of the present invention eliminate various steps utilized by prior art processes. The dilution step which is generally carried out by a customer is no longer required and thus can be eliminated. Other advantages include complete activity against *Aspergillus niger*.

The combination of the phenolic compound disinfectant with a weak organic acid in an aqueous relatively low pH environment containing surfactants and/or solvents unexpectedly has been found to improve results with regard to strong disinfection activity against a broad spectrum of viruses (out of body), bacteria, and fungi. Disinfection is readily achieved where the number of microorganisms killed is a Log reduction of at least 4.0 meaning that less than 1 microorganism in 10,000 remains. Generally Log reductions of at least about 4.0, desirably at least 5.0, and preferably at least about 6.0 are readily achieved by the phenolic disinfectant compositions of the present invention.

Examples of organisms eradicated include various viruses such as Canine parvovirus, Human immunodeficiency virus, Hepatitis virus, Calicivirus, Coronavirus, Rotavirus, and Influenxavirus; various bacteria such as *Escherichia coli, Pseudomonas aeruginosa, Salmonella choleraesuis, Staphylococcus aureus, Micrococcus luteus, Enterococcus hirae, Streptococcus pyogenes,* and *Staphylococcus epidermidis;* and various fungi such as *Penicillium notatus, Trichophyton mentagrophytes,* and *Aspergillus niger.*

An important advantage of the present invention is that the most disinfectant. resistant fungi organism currently known to the world, i.e. *Aspergillus niger* are readily killed. Accordingly, it is believed that the disinfectant compositions of the present invention are effective with regard to a great majority, if not all, of existent viruses, bacteria, and fungi, as set forth in the illustrative examples.

The aqueous phenolic compound disinfectant compositions of the present invention can be generally utilized in any number of applications where disinfection is desired. A typical area of use is in various medical related institutions such as hospitals, clinics, medical centers, pharmaceutical facilities and the like. Other areas include clean rooms, central service areas, and/or any area requiring disinfection. Home uses include disinfection of non-food contact areas including toilets, showers, floors, etc. Objects, items or locations which can be disinfected include floors, countertops, hospital beds, generally any type of apparatus, cabinets, furniture, and the like. Application of the RTU aqueous phenolic disinfectant can be in any conventional manner such as spraying, brushing, applying with a sponge or cloth, flooding and mopping. The ready-to-use aqueous disinfectant compositions can be supplied in any type container such as bottles including spray bottles, aerosols, cans, plastic packages, bulk storage containers (e.g., totes), and the like.

The invention will be better understood by reference to the following examples which serve to illustrate and explain but not to limit the present invention.

EXAMPLE 1

Aqueous Disinfectant Composition Recipe

TABLE 1

| Ingredient | % weight/weight |
| --- | --- |
| OBPCP | 0.032 |
| PTAP | 0.032 |
| Isopropyl Alcohol | 3.150 |
| Dodecylbenzene Sulfonic Acid (DDBSA) | 0.087 |
| Acid | listed |
| WFI (water for injection) | q.s. |

OBPCP is o-benzyl-p-chlorophenol, PTAP is p-t-amyl Phenol q.s. Means Added to Bring to Final Amount The phenolic compound(s), if solid, was dissolved in the solubilizing solvent to form a phenolic compound premix. A surfactant added to water in a separate vessel was then added to the phenolic compound premix and mixed thoroughly. Organic acid or acids were then added and mixed to provide a uniform composition having a pH less than 7 and preferably from about 2 to about 5.

Disinfectant compositions indicated in Table 1 above were formulated in conjunction with organic acids indicated in Table 2 below and diluted with water to provide 100 weight parts water and tested with regard to activity against *Aspergillus niger.* The test method can be described as a suspension test that utilizes 0.56 mL of spores of *Aspergillus niger* added to 5.0 mL of disinfectant. Samples are removed, neutralized and surviving fungi quantitated at appropriate contact times (typically 10 minutes).

TABLE 2

*Aspergillus niger* Reduction

| Formula | Acid | % weight/weight | Log Reduction | Initial Inoculum, Log |
| --- | --- | --- | --- | --- |
| A | No Acid (Control) | 0 | 0.19 | 6.56 |
| B | Formic Acid | 3.0 | 6.56 | 6.56 |
|   | Lactic Acid | 4.0 |   |   |
| C | Formic Acid | 3.0 | 6.56 | 6.56 |
|   | Lactic Acid | 8.0 |   |   |
| D | Formic Acid | 3.0 | 6.56 | 6.56 |
|   | Lactic Acid | 12.0 |   |   |
| E | Glacial Acetic Acid | 4.0 | 6.56 | 6.56 |
|   | Lactic Acid | 13.0 |   |   |
| F | Glacial Acetic Acid | 2.6 | 1.72 | 6.56 |
|   | Lactic Acid | 8.5 |   |   |
| G | Formic Acid | 3.0 | 3.03 | 6.56 |
|   | Lactic Acid | 10.0 |   |   |
| H | Formic Acid | 1.0 | 6.22 | 6.56 |
|   | Lactic Acid | 14.0 |   |   |
|   | Glacial Acetic Acid | 1.0 |   |   |
| I | Formic Acid | 2.0 | 6.56 | 6.56 |
|   | Lactic Acid | 5.0 |   |   |
|   | Glacial Acetic Acid | 2.0 |   |   |
| J | Commercially Available Acid Phenol | — | 0.67 | 6.56 |

Commercial acid phenol contains a concentrated phenol disinfectant containing inorganic acid with a diluted pH between 2 and 3.

As apparent from Table 2, generally a Log deduction of at least 6.0 with regard to the fungi *Aspergillus niger* was often readily achieved in accordance with the present invention.

In a manner similar to Table 1, additional examples were prepared varying the level of phenol and surfactants and the same is set forth in Table 3.

TABLE 3

Examples with varying levels of phenol and different surfactants

| | | % Weight/Weight | | | | | | |
| --- | --- | --- | --- | --- | --- | --- | --- | --- |
| Material | K | L | M | N | O | P | Q | R |
| OBPCP | 0.02983 | 0.02983 | 0.017 | 0.0315 | 0.03318 | 0 | 0 | Commercial |
| PTAP | 0.02802 | 0.02802 | 0.016 | 0.0296 | 0.02955 | 0.05881 | 0.02674 | Acid Phenol |

TABLE 3-continued

Examples with varying levels of
phenol and different surfactants

% Weight/Weight

| Material | K | L | M | N | O | P | Q | R |
|---|---|---|---|---|---|---|---|---|
| Isopropyl Alcohol | 1.44 | 1.44 | 3.6 | 1.52 | 1.52 | 15 | 6.84 | |
| WFI | 77.2 | 77.2 | 86.94 | 88.77 | 81.4 | 67.3 | 71.94 | |
| Fluorosurfactant* | 0.0176 | 0.0176 | 0.01 | 0.018 | 0.018 | 0 | 0 | |
| Lactic acid | 9.1 | 1.96 | 1.24 | 0 | 14.7 | 0 | 0 | |
| Glacial Acetc acid | 0 | 4 | 6.4 | 3.15 | 0 | 4.43 | 10.2 | |
| Formic acid | 12.1 | 8.48 | 1.8 | 6 | 2.6 | 0.415 | 1.13 | |
| DDBSA** | 0 | 0 | 0 | 0 | 0.1 | 12.82 | 9.89 | |

*a Zonyl fluorosurfactant
**DDBSA = Dodecylbenzene sulfonic acid

In a manner similar to that set forth above with regard to Table 2, formulations of Table 3 were tested with respect to *Aspergillus niger* reduction and the results thereof are set forth in Table 4.

TABLE 4

*Aspergillus niger* Reduction regarding formulation of Table 3

| Formula | Log Reduction | Initial Inoculum, Log |
|---|---|---|
| K | 6.14 | 6.14 |
| L | 6.14 | 6.14 |
| M | 6.14 | 6.14 |
| N | 6.14 | 6.14 |
| O | 6.14 | 6.14 |
| P | 6.14 | 6.14 |
| Q | 6.14 | 6.14 |
| R | 0.54 | 6.14 |

As apparent from Tables 3 and 4, the use of different amounts of the phenolic compound and different surfactants always resulted in a Log reduction of at least 6.0 whereas commercial control R did not work.

Table 5 sets forth further examples of the effectiveness of the disinfectant of the present invention wherein the phenolic and surfactant levels were varied. Testing was carried out in a manner similar to Table 2.

As apparent from Table 5, generally a Log reduction of at least 4.0 and usually at least 6.0 were obtained when sufficient amounts of an organic acid were utilized. These reduction levels were significantly more than the commercial acid phenol available product.

The recipe set forth in Table 6 relates to various examples wherein the solvent and the surfactant were varied and testing has similar to that utilized in Table 2.

TABLE 6

Base formula for varying surfactants and co-solvents

Base Formula

| Ingredient | % w/w |
|---|---|
| OBPCP | 0.13997 |
| PTAP | 0.08534 |
| Solvent | 6 |
| Surfactant | X (SEE TABLE 7) |
| WFI | q.s. |
| Glycolic Acid | 14 |

TABLE 5

Additional acid examples and variations in phenol levels and surfactants

| Material | S | T | U | V | W | X | Y | Z | A2 | B2 | C2 |
|---|---|---|---|---|---|---|---|---|---|---|---|
| OBPCP | 0.02068 | 0.06 | 0.03 | 0.0747 | 0.074 | 0.0762 | 0.0242 | 0.0258 | 0.0256 | 0.03365 | Commercial |
| PTAP | 0.02146 | 0 | 0.03 | 0 | 0 | 0 | 0 | 0 | 0 | 0 | Acid |
| Isopropyl Alcohol | 1.245 | 2.81 | 3 | 1.55 | 1.53 | 1.6 | 1.6 | 1.71 | 1.71 | 2.25 | Phenol |
| WFI Water | 90.51 | 94.8 | 92 | 90.3 | 89 | 92.4 | 93.5 | 93 | 93 | 85.8 | |
| DDBSA | 0.0411 | 0.08 | 0.08 | 0.51 | 0.79 | 0.524 | 0.053 | 0.055 | 0.057 | 0.073 | |
| Fluorosurfactant | 0.0076 | 0 | 0 | 0.0154 | 0.0152 | 0.016 | 0 | 0 | 0 | 0 | |
| PAS* | 0.988 | 0 | 0 | 1.18 | 1.17 | 1.21 | 0 | 0 | 0 | 1.5 | |
| Odenone** | 0 | 0 | 0 | 0.086 | 0.084 | 0.088 | 0 | 0 | 0 | 0 | |
| Glacial Acetic Acid | 6.2 | 00 | 5 | 0 | 3.8 | 0 | 2.5 | 1.84 | 3.4 | 4.46 | |
| Formic Acid | 0 | 2.27 | 0 | 5.3 | 3.7 | 4.1 | 2.29 | 3.4 | 1.7 | 0 | |
| Phosphoric Acid | 0 | 0 | 0 | 0 | 0 | 0 | 0 | 0 | 0 | 5.86 | |
| Triethanolamine | 0 | 0 | 0 | 1 | 0 | 0 | 0.02389 | 0.0255 | 0.02559 | 0.03365 | |
| Initial Inoculum Log | 6.11 | 6.11 | 6.11 | 6.92 | 6.92 | 6.92 | 6.92 | 6.92 | 6.92 | 6.92 | 6.92 |
| Log Reduction | 6.11 | 4.02 | 4.2 | 6.92 | 6.92 | 6.92 | 6.92 | 6.92 | 6.92 | 6.92 | 1.08 |

*Alkyl sulfonate coupling agent
**Odor masking agent

TABLE 7

Log Reduction recipe of Table 6

| Solvent | Surfactant Name - Activity | % Active Used | Log Red. | Initial Inoculum, Log |
|---|---|---|---|---|
| n-Propyl Alcohol | Standapol LF - 30% | 1.43 | 6.27 | 6.27 |
| n-Propyl Alcohol | Standapol LF - 30% | 0.3 | 6.27 | 6.27 |
| n-Propyl Alcohol | Standapol LF - 30% | 1 | 6.27 | 6.27 |
| n-Propyl Alcohol | Standapol LF - 30% | 2.5 | 6.27 | 6.27 |
| n-Propyl Alcohol | Burcoterge CSB - 90% | 1.8 | | |
| n-Propyl Alcohol | Lauramine Oxide - 40% | 2.4 | 6.27 | 6.27 |
| n-Propyl Alcohol | SLES - 38% | 0.9 | 6.27 | 6.27 |
| n-Propyl Alcohol | AG 6202 - 50% | 0.2 | 6.27 | 6.27 |
| | Burcoimidozoline - 90% | 1.0 | | |
| n-Propyl Alcohol | Burcoterge LFE 1000 - 100% | 0.71 | 6.27 | 6.27 |
| n-Propyl Alcohol | Deterge LF 7315 - 50% | 0.5 | 6.27 | 6.27 |
| | Deteric CEP - 50% | 2.45 | | |
| | Deterge AT 100 - 100% | 2.76 | | |
| n-Propyl Alcohol | Dowfax 8390 - 35% | 1.1 | 6.27 | 6.27 |
| n-Propyl Alcohol | Colatrope 555 - 40% | 0.64 | 6.27 | 6.27 |
| | Deriphat 160C - 30% | 0.2 | | |
| | DV 6836 | 3.9 | | |
| isopropyl Alcohol | Miranol JEM - 40% | 2.2 | 6.27 | 6.27 |
| | Rhodapon BOS - 40% | 1.6 | | |
| | Standapol LF - 33% | 0.22 | | |
| isopropyl Alcohol | Sulfotex OA - 40% | 0.88 | 6.27 | 6.27 |
| isopropyl Alcohol | Monatrope 1250A - 45% | 1.4 | 6.27 | 6.27 |
| | Cocamide DEA | 0.8 | | |
| | Sulfotex OA - 40% | 2.7 | | |
| isopropyl Alcohol | Mackam 75/2C - 39% | 3.1 | 6.27 | 6.27 |
| isopropyl Alcohol | Mackam 2CYSF - 50% | 3 | 6.27 | 6.27 |
| isopropyl Alcohol | Mackam CBS 50 - 50% | 3 | 5.62 | 6.27 |
| isopropyl Alcohol | Mackam JS - 49% | 5 | 6.27 | 6.27 |
| isopropyl Alcohol | Mackam OAB - 37% | 3 | 5.45 | 6.27 |
| isopropyl Alcohol | Septosol SB-D | | | |
| | Rhodacal DSB - 45% | 0.15 | 5.62 | 6.27 |
| | Deriphat 151C - 45% | 0.06 | | |
| | SLES - 38% | 2.8 | | |
| isopropyl Alcohol | Mackamine C8 - 40% | 1.2 | 6.24 | 6.24 |
| isopropyl Alcohol | Petro ULF - 50% | 3.4 | 6.24 | 6.24 |
| isopropyl Alcohol | Biosoft S 101 - 97% | 0.4 | 6.24 | 6.24 |
| isopropyl Alcohol | Miranol JEM - 40% | 2.1 | 6.24 | 6.24 |
| | Lauramine Oxide - 30% | 0.63 | | |
| isopropyl Alcohol | AO 728 - 50% | 0.8 | 5.74 | 6.24 |
| 1-Butoxyethanol | Lauramine Oxide - 30% | 0.5 | 6.27 | 6.27 |
| Dowanol EB | Lauramine Oxide - 30% | 0.1 | 6.27 | 6.27 |
| | SLES - 38% | 0.2 | | |
| | Mackam 2CYSF - 50% | 1 | | |
| Dowanol EB | Avenal S-74 - 35% | .33 | 6.24 | 6.24 |
| *Dowanol EB | Mackamine C8-Octyl - 40% | .78 | 6.24 | 6.24 |
| Dowanol EB | Standapol LF - 30% | .97 | 6.24 | 6.24 |
| Dowanol EB | Biosoft S 101 - 97% | .66 | 6.24 | 6.24 |
| Dowanol EB | Mackam BW139 - 40% | 2.1 | 6.24 | 6.24 |
| | Petro ULF - 50% | 1.5 | | |
| Hexylene Glycol | Lauramine Oxide - 30% | 0.41 | 5.42 | 6.27 |
| Hexylene Glycol | Mackam 2CYSF - 50% | 0.3 | 4.92 | 6.27 |
| | SLES - 38% | 0.5 | | |
| Hexylene Glycol | Mirataine ASC - 50% | 1 | 577 | 6.27 |
| Hexylene Glycol | Rhodapon BOS - 40% | 3.3 | 6.27 | 6.27 |
| Hexylene Glycol | Standapol LF - 30% | 0.71 | 6.27 | 6.27 |
| Diethyleneglycol monoethylether | AO 728 - 50% | 2.7 | 5.77 | 6.27 |
| Diethylene glycol monoethyl ether | Colonial ZF 20 - 50% | 1.1 | 6.27 | 6.27 |
| | Colafax PE 3373 - 100% | 8.0 | | |
| | Colafax PE 3371 - 50% | 3.9 | | |
| M Pyrol (N-methyl-2-pyrolidone) | Lauramine Oxide - 30% | 0.21 | 5.53 | 6.27 |
| M Pyrol | SLES - 38% | 0.22 | 5.12 | 6.27 |
| | Lauramine Oxide - 30% | 1.2 | | |
| M Pyrol | Mackam OAB - 37% | 0.28 | 4.88 | 6.27 |
| M Pyrol | Rhodacal DSB - 45% | 0.34 | 4.79 | 6.27 |
| M Pyrol | Mackamine C8 - 40% | 1.8 | 6.24 | 6.24 |
| M Pyrol | Miranol JEM - 40% | 0.22 | 5.24 | 6.24 |
| | Mackam CBS 50 - 50% | 2.5 | | |
| M Pyrol | Mackam OAB - 37% | 1.37 | 6.24 | 6.24 |
| | Lauramine Oxide - 30% | 0.86 | | |
| M Pyrol | Mackam JS - 49% | 0.56 | 6.24 | 6.24 |
| | Lauramine Oxide - 30% | 0.44 | | |
| M Pyrol | Mackam 2CYSF - 50% | 0.32 | 6.24 | 6.24 |
| | Lauramine Oxide - 30% | 0.5 | | |

TABLE 7-continued

Log Reduction recipe of Table 6

| Solvent | Surfactant Name - Activity | % Active Used | Log Red. | Initial Inoculum, Log |
|---|---|---|---|---|
| M Pyrol | Gemtex DpNP Carboxylated surfactant in propylene glycol ethers 36% solids | 0.83 | 6.24 | 6.24 |
| M Pyrol | M Pyrol (N-methyl-2-pyrolidone) Lauramine Oxide - 30% nonionic | 0.7 | 5.74 | 6.24 |
| M Pyrol | Surfedon LP 300 Lauramine Oxide - 30% | 1.1 | 6.24 | 6.24 |
| M Pyrol | Phenoxy ethanol Lauramine Oxide - 30% | 0.93 | 6.24 | 6.24 |
| M Pyrol | Amphoteric 400 - 40% | | 3.99 | 6.24 |
| Diethylene glycol monobutyl ether | Lauramine Oxide - 30% | 0.17 | 5.77 | 6.27 |
| Diethylene glycol monobutyl ether | Mackam 2CYSF - 50% | 1.9 | 5.53 | 6.27 |
| Diethylene glycol monobutyl ether | Standapol LF - 30% | 0.8 | 5.32 | 6.24 |
| Diethylene glycol monobutyl ether | AO 728 - 50% | 0.84 | 6.24 | 6.24 |
| Diethylene glycol monobutyl ether | Petro ULF - 50% | 1.9 | 6.24 | 6.24 |
| Diethylene glycol monobutyl ether | Sulfotex OA - 40% | 1.6 | 6.24 | 6.24 |
| Diethylene glycol monobutyl ether | Biosoft S 101 - 97% | 0.54 | 5.74 | 6.24 |
| Diethylene glycol monobutyl ether | SLES - 38% | 0.62 | 6.24 | 6.24 |
| Diethylene glycol monobutyl ether | Mackam BW 139 - 50% | 2.6 | 6.24 | 6.24 |
| Dipropylene glycol methyl ether | Mackamine C8 - 40% | 2.7 | 4.85 | 6.24 |
| Dipropylene glycol monomethyl ether | Biosoft S 101 - 97% - anionic | 0.2 | 4.89 | 6.24 |
| *50/50 Surfedon LP 100/EG | Lauramine Oxide - 30% | 2.1 | 6.27 | 6.27 |
| 50/50 Surfedon LP 100/EG | Rhodacal DSB - 45% Lauramine Oxide - 30% | 0.17 0.5 | 6.27 | 6.27 |
| 50/50 Surfedon LP 100/EG | Mackamine C8 - 40% Avenal S-74 - 35% | 0.64 0.34 | 6.24 | 6.24 |
| 50/50 Surfedon LP 100/EG | AO 728 - 50% | 0.84 | 6.24 | 6.24 |
| 50/50 Surfedon LP 100/EG | Mackam BW 139 - 50% | 2.2 | 6.24 | 6.24 |
| 50/50 Surfedon LP 100/EG | Biosoft S 101 - 97% | 0.24 | 6.24 | 6.24 |
| 50/50 Surfedon LP 100/EG | Standapol LF - 30% | 0.66 | 6.24 | 6.24 |
| 50/50 Surfedon LP 100/EG | Petro ULF - 50% | 2 | 6.24 | 6.24 |

In the above table DOWANOL EB is (Diethylene glycol n-butyl ether), SURFEDON LP 100 is (N-alkylpyrrolidone—a nonionic surfactant/solvent) and EG is (ethylene glycol). The above listed surfactants in Table 6 are known to the art and to the literature and a chemical description thereof can be found in the above-noted 2003 McCutheon's Volume 1: Emulsifiers and Detergents Handbook.

As apparent from Table 7, when sufficient amounts of the surfactant was utilized, the log reduction of at least about 5 and typically at least 6.0 against *Aspergillus niger* were duly obtained.

In Table 8, the various formulations wherein generally different alcohols and different acids were utilized, were tested with respect to *Aspergillus niger* reduction.

TABLE 8

| Ingredient | Amount, % weight/weight | | | | | | | | | | |
|---|---|---|---|---|---|---|---|---|---|---|---|
| OPP | 0.15 | 0.30 | 0.30 | 0.30 | 0.30 | 0.30 | 0.30 | 0.30 | 0.30 | 0.30 | 0.15 |
| OBPCP | 0.15 | — | — | — | — | — | — | — | — | — | 0.15 |
| Rhodacal DSB* | 1.50 | 1.50 | 1.50 | 1.33 | 1.33 | 1.33 | 1.33 | 1.33 | 1.33 | 1.33 | 3.00 |
| Zonyl Fluorosurfactant | 0.02 | 0.02 | 0.02 | 0.02 | 0.02 | 0.02 | 0.02 | 0.02 | 0.02 | 0.02 | 0.02 |
| Isopropyl Alcohol | — | 2.00 | — | 4.00 | 4.00 | 4.00 | — | — | — | — | 5.00 |
| n-Propyl Alcohol | 4.0 | — | 2.00 | — | — | — | 4.00 | 6.00 | 12.00 | 2.00 | — |
| Acetic Acid | 4.0 | 4.0 | 4.00 | 1.00 | 4.00 | — | 1.00 | 1.00 | 3.00 | 4.00 | 3.00 |
| Propionic Acid | — | — | — | 2.00 | — | 4.00 | 2.00 | — | — | — | — |
| Benzoic Acid | — | — | — | — | — | — | — | — | — | — | 0.30 |
| M-Pyrol | — | 2.00 | 2.00 | — | — | — | — | — | — | 2.00 | — |
| Water | q.s. | q.s. | q.s. | q.s. | q.s. | q.s. | q.s. | q.s. | q.s. | q.s. | q.s. |
| Log | 6.44 | 6.44 | 6.44 | 6.68 | 6.68 | 6.68 | 6.68 | 6.68 | 6.68 | 6.68 | 6.68 |

TABLE 8-continued

| Ingredient | Amount, % weight/weight | | | | | | | | | |
|---|---|---|---|---|---|---|---|---|---|---|
| Reduction (Initial inoculum) | (6.44) | (6.44) | (6.44) | (6.68) | (6.68) | (6.68) | (6.68) | (6.68) | (6.68) | (6.68) |

Once again, the phenol compositions of the present invention prove very effective in achieving a log reduction of at least 6.0 with respect to the fungi *Aspergillus niger*.

While gamma radiation is optional, various samples were tested at dosage ranges of 15 to 20 KGy and from 30 to 40 KGy. The samples were irradiated in a $^{60}$Co research reactor. The doses were controlled by adjusting exposure times and confirmed by dosimetry. Formulations for radiation treatment are set forth in Table 9.

TABLE 9

Formulas - Irradiation

| Material | % Weight/Weight | | |
|---|---|---|---|
| | E2 | F2 | G2 |
| OBPCP | 0.140 | 0.139 | 0.140 |
| PTAP | 0.0865 | 0.0864 | 0.0864 |
| Hexylene Glycol | 5.97 | 5.88 | 5.96 |
| MilliQ Water | 66.8185 | 66.9046 | 65.6836 |
| Glycolic Acid | 13.97 | 14.22 | 14.22 |
| Bioterge PAS (Octyl sulfate) | 6.1 | 5.88 | 5.89 |
| Isopropyl Alcohol | 6.1 | 6.1 | 7.1 |
| Lauramine oxide | 0.815 | 0.31 | 0.92 |
| *SLES | 0 | 0.48 | 0 |

*Sodium lauryl ether sulfate

After radiation, the compositions of Table 9 were tested against the fungi *Aspergillus niger*. In each of the three examples, a Log reduction of at least 6.0 was achieved. Surprisingly, gamma radiation did not destroy the effectiveness of the acidic aqueous disinfectant compositions of the present invention.

As readily apparent from the above examples, the aqueous disinfectant composition of the present invention was completely effective against *Aspergillus niger*.

Controls

Various conventional disinfectant compositions were prepared as controls which contained the following ingredients:

Acid Concentrate A—water, phenol, surfactant and phosphoric acid, a commercially available product.

Acid Concentration B—water, surfactant, phenol and phosphoric acid, a commercially available product.

White Vinegar—5% acetic acid

Mixture for an Aerosol Container—a mixture of ethyl alcohol, and phenol, a commercially available product.

Alakine Concentration A—phenol and potassium hydroxide, a commercially available product.

Alakine Concentration B—phenol and potassium hydroxide, a commercially available product.

When tested against *Aspergillus niger*, the Log reduction for acidic concentrations A and B were only about 0.6. The white vinegar solution gave a Log reduction of approximately 2.2. The aerosol mixture had a Log reduction of approximately 1.7 whereas the alakine concentration A and B gave respective Log reductions of approximately 2.4 and 1.0. Accordingly, conventional disinfectant solutions were not effective against *Aspergillus niger*.

While in accordance with the Patent Statutes, the best mode and preferred embodiments have been set forth, the scope of the invention is not limited thereto, but rather by the scope of the attached claims.

What is claimed is:

1. A ready to use aqueous disinfectant composition, comprising:
   water, wherein all parts are based upon 100 parts by weight of water;
   a total of from about 0.005 to 0.3 parts by weight of two or more phenolic compounds, wherein at least one of the phenolic compounds is an aromatic substituted phenol and wherein at least one of the phenolic compounds is an aliphatic substituted phenol;
   a total of from 3.0 to 30 parts by weight of an alcohol, wherein said alcohol is an alkyl alcohol having from 1 to about 10 carbon atoms or a glycol alcohol having from 2 to about 12 carbon atoms or a combination thereof; and
   a total of from 0.5 to about 30 parts by weight of two or more organic carboxylic acids, wherein at least one of the organic acids consists of an aliphatic monocarboxylic acid having from 1 to about 10 carbon atoms, and wherein the aqueous disinfectant composition has a pH from about 2 to 5.

2. The ready to use aqueous disinfectant composition according to claim 1, wherein the amount of said two or more phenolic compounds is from about 0.007 to 0.3 parts by weight.

3. The ready to use aqueous disinfectant composition according to claim 2, wherein the amount of said two or more organic carboxylic acids is from about 2 to about 20 parts by weight, and wherein said organic carboxylic acids each have a pKa from about 1 to about 6.5; wherein the composition further includes a surfactant, wherein said surfactant is an anionic surfactant, a cationic surfactant, a nonionic surfactant, or an amphoteric surfactant, or combinations thereof, and wherein the amount of said surfactant is from about 0.01 to about 15 parts by weight.

4. The ready to use aqueous disinfectant composition according to claim 3, wherein said aliphatic substituted phenol has at least one substituent group comprising a hydrocarbon group having from 1 to about 20 carbon atoms, wherein said organic acid consisting of the aliphatic monocarboxylic acid is formic acid, acetic acid, propionic acid, butyric acid, isobutyric acid, valeric acid, isovaleric acid, or combinations thereof, and wherein the amount of said two or more organic carboxylic acids is from about 5 to about 17 parts by weight.

5. The ready to use aqueous disinfectant composition according to claim 4, wherein said aliphatic substituted phenol is p-chloro-m-xylenol or p-t-amylphenol or a combination thereof, wherein the aromatic substituted phenol is o-phenylphenol, o-benzyl-p-chlorophenol or 5-chloro-2-(2, 4-dichlorophenoxy)phenol, or combinations thereof, and wherein the amount of phenolic compounds is from about 0.01 to about 0.2 parts by weight.

6. The ready to use disinfectant composition according to claim 5, wherein said alcohol is isopropyl alcohol or n-propyl alcohol or combinations thereof in amount of from about 1 to about 20 parts by weight, and wherein the amount of said surfactant is from about 0.05 to about 3 parts by weight.

7. The ready to use aqueous disinfectant composition of claim 1, which is capable of a Log reduction of at least 4.0 with regard to *Aspergillus niger*.

8. The ready to use aqueous disinfectant composition of claim 5, which is capable of a Log reduction of at least 6.0 with regard to *Aspergillus niger*.

9. The ready to use aqueous disinfectant composition of claim 1, wherein at least one of the organic carboxylic acids consists of a hydroxyl group containing carboxylic acid.

10. The ready to use aqueous disinfectant composition of claim 9, wherein the phenolic compounds comprise o-benzyl-p-chlorophenol and p-t-amylphenol.

11. The ready to use aqueous disinfectant composition according to claim 9, which is capable of a Log reduction of at least 4.0 with regard to *Aspergillus niger*.

12. The ready to use aqueous disinfectant composition according to claim 10, which is capable of a Log reduction of at least 6.0 with regard to *Aspergillus niger*.

13. The ready to use aqueous disinfectant composition according to claim 1, which has been irradiated.

14. The ready to use aqueous disinfectant composition according to claim 5, which has been irradiated.

15. A process for preparing a ready to use aqueous disinfectant phenolic composition, comprising the steps of:
adding and mixing water, two or more phenolic compounds, at least one alcohol; and two or more organic carboxylic acids;
the total amount of said two or more phenolic compounds being from about 0.005 to 0.3 parts per 100 parts by weight of water, wherein at least one of the phenolic compounds is an aromatic substituted phenol and wherein at least one of the phenolic compounds is an aliphatic substituted phenol, the total amount of said alcohol being from 3.0 to 30 parts per 100 parts by weight of water, wherein said alcohol is an alkyl alcohol having from 1 to about 10 carbon atoms or a glycol alcohol having from 2 to about 12 carbon atoms or a combination thereof, and
a total of from 0.5 to about 30 parts by weight of said two or more organic carboxylic acids per 100 parts by weight of water, wherein at least one of the organic acids consists of an aliphatic monocarboxylic acid having from 1 to about 10 carbon atoms, and wherein said aqueous disinfectant composition has a pH of from about 2 to 5.

16. The process according to claim 15, wherein the amount of said two or more phenolic compounds is from about 0.007 to about 0.3 parts by weight.

17. The process according to claim 16, wherein the amount of said two or more organic carboxylic acids is from about 2 to about 20 parts by weight, and wherein said organic carboxylic acids each have a pKa from about 1 to about 6.5; wherein said phenolic composition further includes a surfactant, wherein said surfactant is an anionic surfactant, a cationic surfactant, a nonionic surfactant, or an amphoteric surfactant, or combinations thereof, and wherein the amount of said surfactant is from about 0.01 to about 15 parts by weight per 100 parts by weight of water.

18. The process according to claim 17, wherein said aliphatic substituted phenol has at least one substituent group comprising a hydrocarbon group having from 1 to about 20 carbon atoms, wherein said organic acid consisting of the aliphatic monocarboxylic acid is formic acid, acetic acid, propionic acid, butyric acid, isobutyric acid, valeric acid, isovaleric acid, or combinations thereof, and wherein the amount of said two or more organic carboxylic acids is from about 5 to about 17 parts by weight.

19. The process according to claim 18, wherein said aliphatic substituted phenol is p-chloro-m-xylenol, or p-t-amylphenol, or a combination thereof, wherein the aromatic substituted phenol is o-phenylphenol, o-benzyl-p-chlorophenol, or 5-chloro-2-(2,4-dichlorophenoxy)phenol, or combinations thereof, and wherein the amount of phenolic compounds is from about 0.01 to about 0.2 parts by weight, and wherein said alcohol is isopropyl alcohol or n-propyl alcohol or combinations thereof in amount of from about 1 to about 20 parts by weight, and wherein the amount of said surfactant is from about 0.05 to about 3 parts by weight.

20. The process according to claim 17, including mixing said surfactant and said water, and separately mixing said two or more phenolic compounds and said alcohol, and subsequently combining said surfactant-water mixture and said phenolic-alcohol mixture, and subsequently adding said organic acids to said combined mixtures.

21. The process according to claim 18, including mixing surfactant and said water, and separately mixing said two or more phenolic compounds and said alcohol, and subsequently combining said surfactant-water mixture and said phenolic-alcohol mixture, and subsequently adding said organic acids to said combined mixtures.

22. The process according to claim 19, including mixing surfactant and said water, and separately mixing said two or more phenolic compounds and said alcohol, and subsequently combining said surfactant-water mixture and said phenolic-alcohol mixture, and subsequently adding said two or more organic acids to said combined mixtures.

23. The process of claim 15, wherein the composition is capable of a Log reduction of at least 4.0 with regard to *Aspergillus niger*.

24. The process of claim 19, wherein the composition is capable of a Log reduction of at least 5.0 with regard to *Aspergllus niger*.

25. The process of claim 20, wherein the composition is capable of a Log reduction of at least 6.0 with regard to *Aspergilius niger*.

26. The process of claim 22, wherein the composition is capable of a Log reduction of at least 6.0 with regard to *Aspergillus niger*.

27. The process according to claim 15, wherein the phenolic compounds comprise o-benzyl-p-chlorophenol and p-t-amylphenol, and wherein at least one of the organic carboxylic acids consists of a hydroxyl group containing carboxylic acid.

28. The process according to claim 19, wherein the phenolic compounds comprise o-benzyl-p-chlorophenol and p-t-amylphenol.

29. The process according to claim 22, wherein the phenolic compounds comprise o-benzyl-p-chlorophenol and p-t-amylphenol, and wherein at least one of the organic carboxylic acids consists of a hydroxyl group containing carboxylic acid.

30. The process for preparing a phenolic disinfectant composition according to claim 15, including irradiating said phenolic composition.

31. The process for preparing a phenolic disinfectant composition according to claim 22, including irradiating said phenolic composition.

32. The process for preparing a phenolic disinfectant composition according to claim 27, including irradiating said phenolic composition.

33. The process for preparing a phenolic disinfectant composition according to claim 29, including irradiating said phenolic composition.

34. An aqueous disinfectant composition, consisting essentially of:
   water, wherein all parts are based upon 100 parts by weight of water;
   a total of from 0.005 to 5 parts by weight of two or more phenolic compounds, wherein at least one of the phenolic compounds is an aromatic substituted phenol and wherein at least one of the phenolic compounds is an aliphatic substituted phenol;
   a total of from 1.5 to 15 parts by weight of an alcohol, wherein said alcohol is an alkyl alcohol having from 1 to 10 carbon atoms or a glycol alcohol having from 2 to 12 carbon atoms or a combination thereof;
   a total of from 0.01 to 15 parts by weight of a surfactant, wherein said surfactant is an anionic surfactant, a cationic surfactant, a nonanionic surfactant, or an amphoteric surfactant, or combinations thereof; and
   a total of from 5 to 30 parts by weight of two or more organic carboxylic acids, and wherein the aqueous disinfectant composition has a pH from 2 to 5.

35. The aqueous disinfectant composition according to claim 34, wherein the amount of said phenolic compound is from 0.007 to 0.3 parts by weight, wherein at least one of the organic carboxylic acids consists of an aliphatic monocarboxylic acid having from 1 to about 10 carbon atoms, and wherein at least one of the organic carboxylic acids consists of a hydroxyl group containing carboxylic acid.

36. The aqueous disinfectant composition according to claim 35, wherein the amount of said organic carboxylic acids is from 2 to 20 parts by weight, and wherein said organic carboxylic acids each have a pKa from 1 to 6.5; and wherein the amount of said surfactant is from 0.02 to 10 parts by weight.

37. The aqueous disinfectant composition according to claim 36, wherein said aliphatic substituted phenol has at least one substituent group comprising a hydrocarbon group having from 1 to 20 carbon atoms, wherein said organic acid consisting of the aliphatic monocarboxylic acid is formic acid, acetic acid, propionic acid, butyric acid, isobutyric acid, valeric acid, isovaleric acid, or combinations thereof, and wherein the amount of said two or more organic carboxylic acids is from 5 to 17 parts by weight.

38. The aqueous disinfectant composition according to claim 37, wherein said aliphatic substituted phenol is p-chloro-m-xylenol or p-t-amylphenol, or a combination thereof, wherein the aromatic subsitituted phenol is o-phenylphenol, o-benzyl-p-chlorophenol, or 5-chloro-2-(2,4-dichlorophenoxy)phenol, or combinations thereof, and wherein the amount of said phenolic compounds is from 0.01 to 0.2 parts by weight.

39. The aqueous disinfectant composition according to claim 38, wherein said alcohol is isopropyl alcohol or n-propyl alcohol or combinations thereof in amount of from 1.5 to 8 parts by weight, and wherein the amount of said surfactant is from 0.05 to 3 parts by weight.

40. The aqueous disinfectant composition according to claim 39, wherein the amount of said organic carboxylic acids is from 2 to 20 parts by weight, wherein said organic carboxylic acids each have a pKa from 1 to 6.5; and wherein the surfactant is a fluorosurfactant.

41. The aqueous disinfectant composition according to claim 34, wherein the surfactant is a fluorosurfactant, and wherein said phenolic compounds comprise o-benzyl-p-chlorophenol and p-t-amylphenol, and wherein the amount of said phenolic compounds is from 0.007 to 0.2 parts by weight.

* * * * *

UNITED STATES PATENT AND TRADEMARK OFFICE
CERTIFICATE OF CORRECTION

| | | |
|---|---|---|
| PATENT NO. | : 7,144,846 B2 | Page 1 of 1 |
| APPLICATION NO. | : 10/843600 | |
| DATED | : December 5, 2006 | |
| INVENTOR(S) | : Shahin Keller et al. | |

It is certified that error appears in the above-identified patent and that said Letters Patent is hereby corrected as shown below:

Column 18,

Claim 24, line 3, please correct the word "Asperglllus", should be --Aspergillus--

Claim 25, line 3, please correct the word "Aspergilius", should be --Aspergillus--

Signed and Sealed this

Twentieth Day of February, 2007

JON W. DUDAS
*Director of the United States Patent and Trademark Office*